(12) United States Patent
Ries

(10) Patent No.: US 7,173,507 B2
(45) Date of Patent: Feb. 6, 2007

(54) MAGNET COIL SYSTEM FOR CONTACTLESS MOVEMENT OF A MAGNETIC BODY IN A WORKING SPACE

(75) Inventor: Günter Ries, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 326 days.

(21) Appl. No.: 10/934,738

(22) Filed: Sep. 7, 2004

(65) Prior Publication Data

US 2005/0052178 A1    Mar. 10, 2005

(30) Foreign Application Priority Data

Sep. 5, 2003 (DE) ................ 103 40 925

(51) Int. Cl.
*H01F 5/00* (2006.01)
(52) U.S. Cl. ................................... 335/299
(58) Field of Classification Search ............... 335/299
See application file for complete search history.

(56) References Cited

U.S. PATENT DOCUMENTS

| | | | | |
|---|---|---|---|---|
| 4,585,282 | A * | 4/1986 | Bosley | 310/90.5 |
| 4,874,346 | A * | 10/1989 | Wachspress | 446/484 |
| 4,959,613 | A | 9/1990 | Yamamoto et al. | |
| 5,125,888 | A | 6/1992 | Howard et al. | |
| 5,332,987 | A * | 7/1994 | Hennessy et al. | 335/216 |
| 5,365,927 | A | 11/1994 | Roemer et al. | |
| 5,406,205 | A | 4/1995 | Müller | |
| 5,779,694 | A * | 7/1998 | Howard et al. | 604/891.1 |
| 6,241,671 | B1 | 6/2001 | Ritter et al. | |
| 6,475,223 | B1 * | 11/2002 | Werp et al. | 606/108 |
| 6,529,761 | B2 | 3/2003 | Creighton, IV et al. | |
| 6,636,757 | B1 * | 10/2003 | Jascob et al. | 600/424 |
| 6,885,266 | B2 * | 4/2005 | Ochi-Okorie | 335/296 |

FOREIGN PATENT DOCUMENTS

| | | |
|---|---|---|
| DE | 3907141 A1 | 9/1989 |
| DE | 3937148 C2 | 6/1993 |
| DE | 4313843 A1 | 11/1994 |
| DE | 4438584 A1 | 5/1995 |
| DE | 10142253 C1 | 4/2003 |
| GB | 1035205 | 7/1966 |
| WO | WO94/24934 | 11/1994 |
| WO | WO96/03795 A1 | 2/1996 |
| WO | WO00/13586 | 3/2000 |

OTHER PUBLICATIONS

Meeker et al., "Optimal Realization of Arbitrary Forces in a Magnetic Streotaxis System", IEEE Transactions on Magnetics, vol. 32, No. 2, Mar. 1996, pp. 320-328.
Mosse et al., "Electrical Stimulation for Propelling Endoscopes", Gastrointestinal Endoscopy, vol. 54, No. 1, 2001, pp. 79-83.

* cited by examiner

*Primary Examiner*—Ramon M. Barrera
(74) *Attorney, Agent, or Firm*—Staas & Halsey LLP

(57) ABSTRACT

A magnetic body is to be moved in a contactless fashion in a working space with the aid of the magnet coil system composed of fourteen individually drivable individual coils. The coil system is to be used for this purpose to produce three magnetic field components and five magnetic field gradients. The individual coils are preferably arranged on end-face or lateral surfaces situated oppositely in pairs, and on a tubular peripheral surface surrounding the working space.

26 Claims, 11 Drawing Sheets

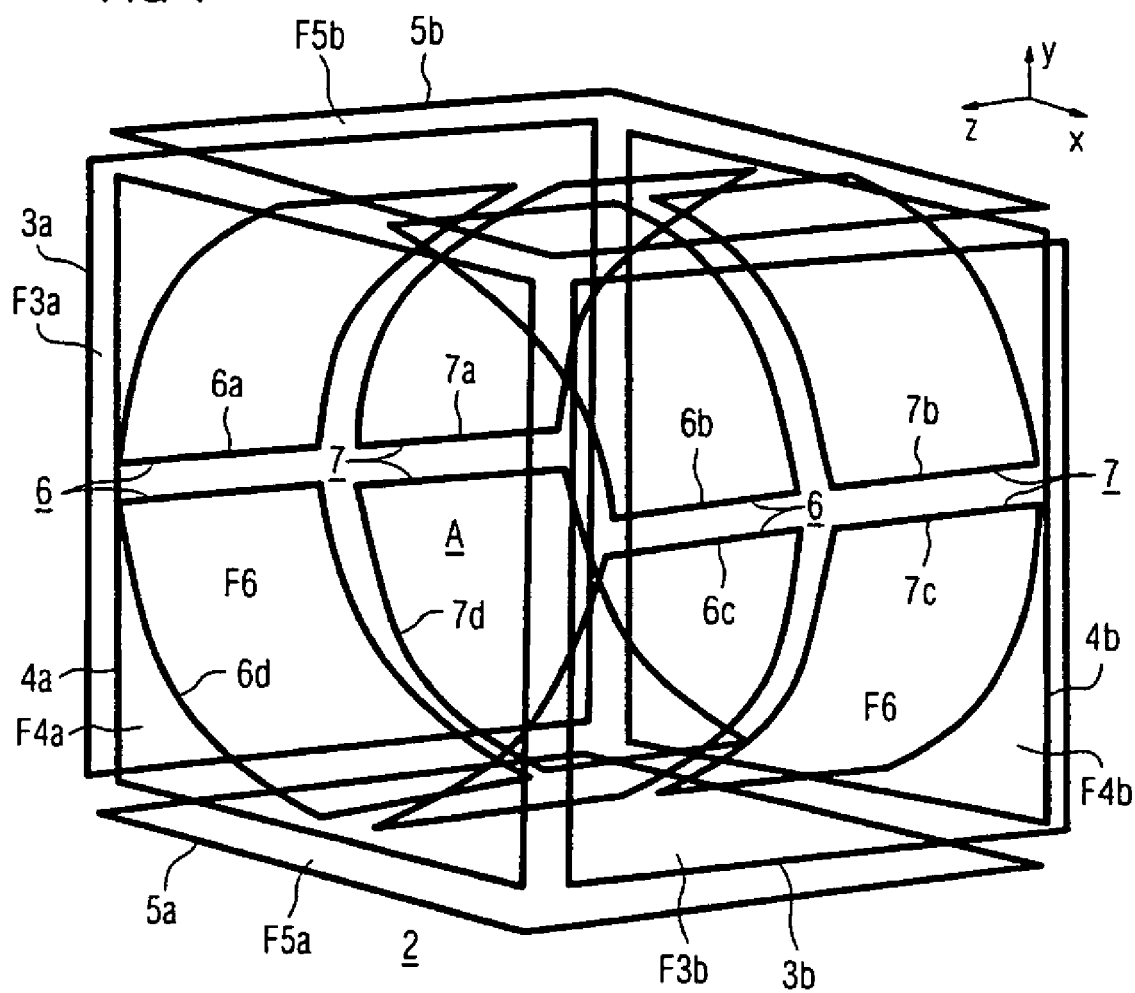

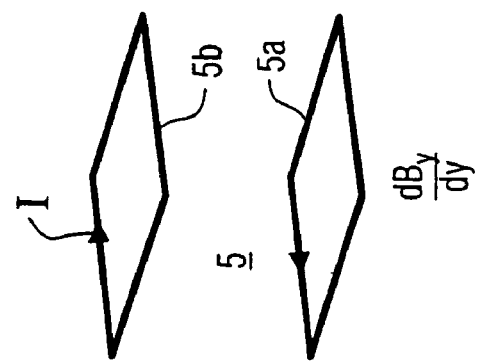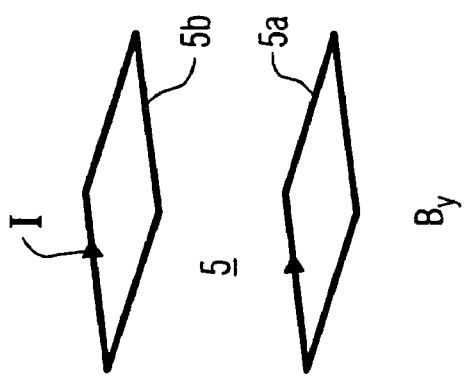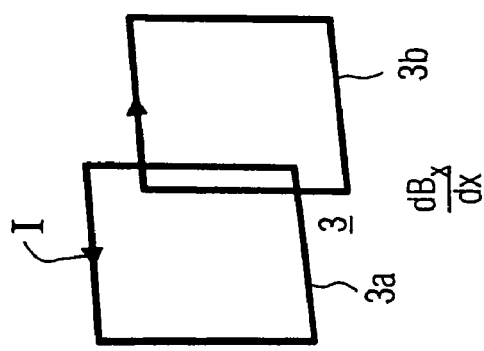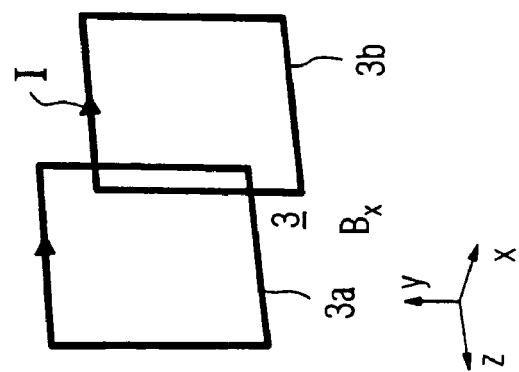

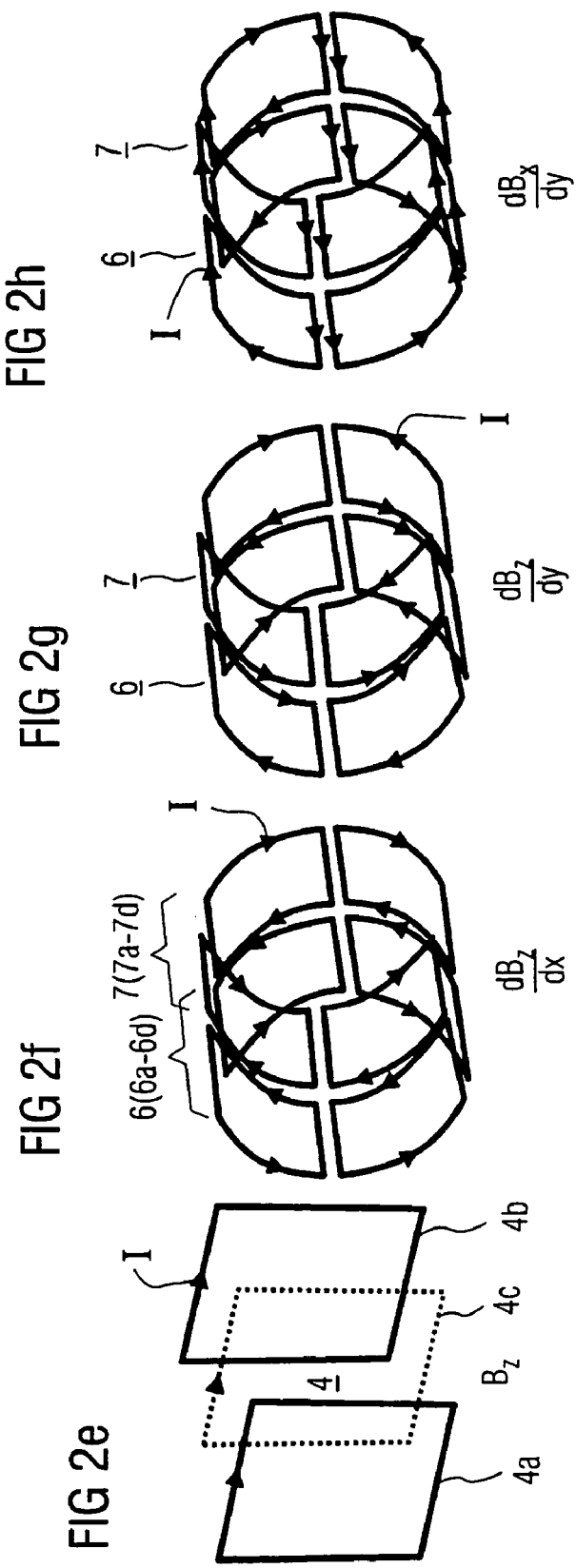

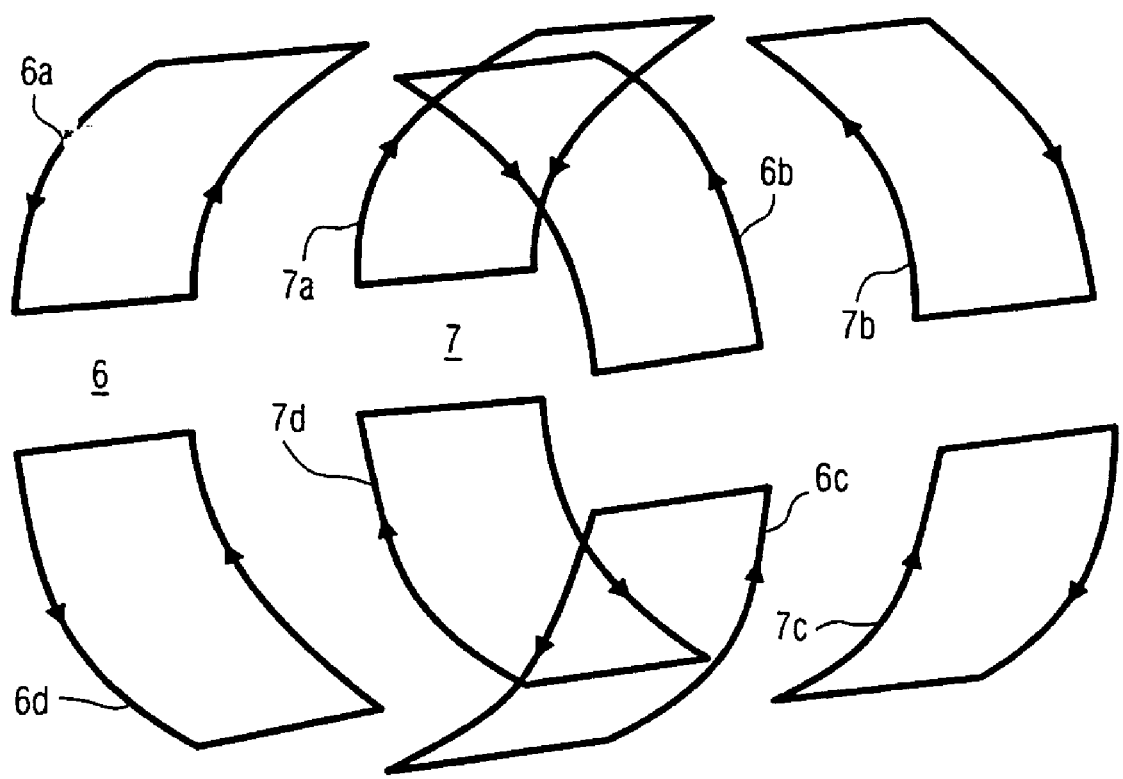

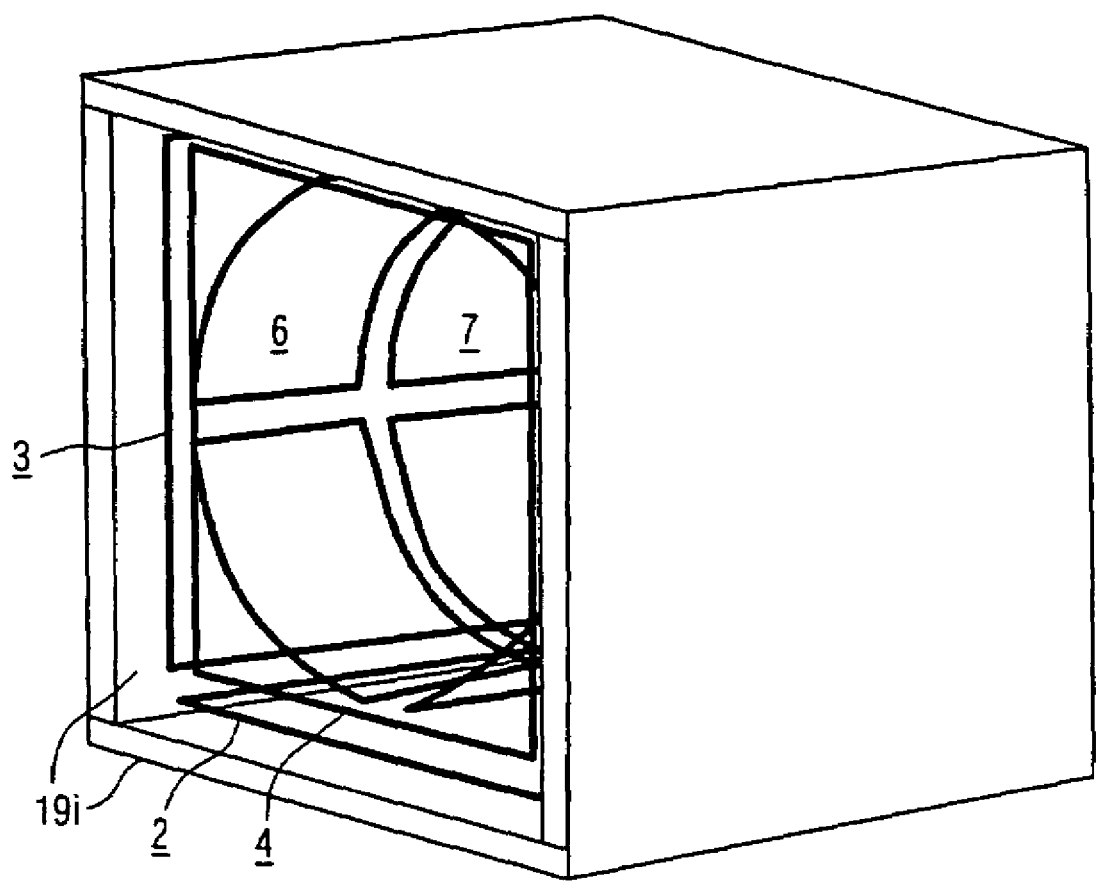

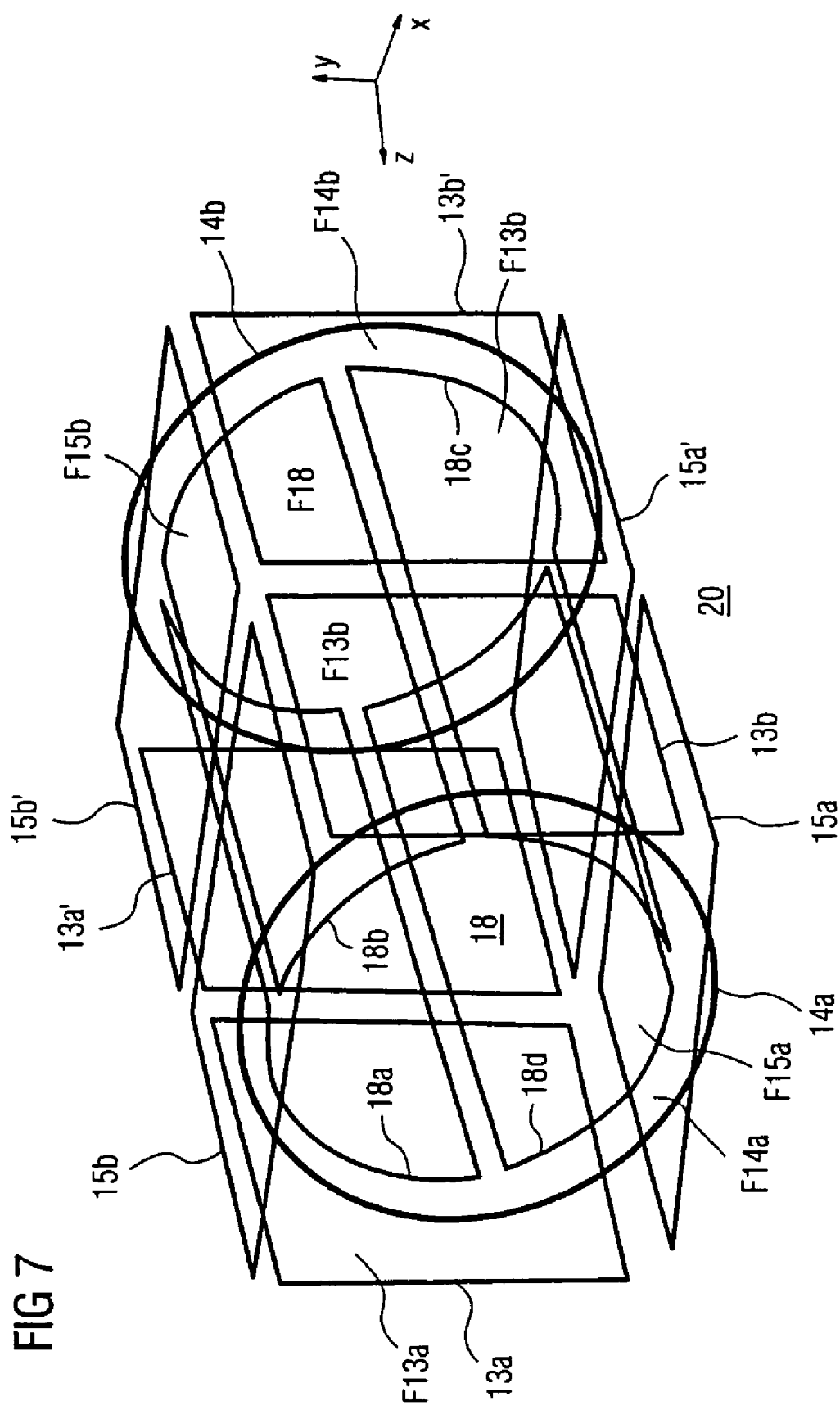

MAGNET COIL SYSTEM FOR CONTACTLESS MOVEMENT OF A MAGNETIC BODY IN A WORKING SPACE

CROSS REFERENCE TO RELATED APPLICATIONS

This application is based on and hereby claims priority to German Application No. 10340925.4 filed on Sep. 5, 2003, the contents of which are hereby incorporated by reference.

BACKGROUND OF THE INVENTION

The invention relates to a magnet coil system having a plurality of individually drivable individual coils for contactless movement of a magnetic body in a three-dimensional working space that is surrounded by surfaces defined in a rectangular x,y,z coordinate system. Such a magnet coil system is to be gathered from "*IEEE Transactions on Magnetics*", Vol. 32, No. 2, March 1996, pages 320 to 328.

Use is made in medicine of endoscopes and catheters that are introduced via incisions or body orifices, and can be displaced in a longitudinal direction from outside and can thus be navigated only in one dimension. Light guides permit optical inspection, it being possible to use control wires to rotate an endoscope pipe and thus the viewing direction. It is possible thereby to construct devices for biopsies, in particular. However, the probes used in this case can be navigated only in limited fashion, particularly at branching points, and so contactless exertion of force from outside could be attended by an expansion of the field of application.

The publication mentioned at the beginning and U.S. Pat. No. 5,125,888 A disclose a magnet coil system for contactless magnetic control of a probe comprising six preferably superconducting individual coils which are arranged on the faces of a cube whose position is to be described mathematically in a rectangular x,y,z coordinate system. The aim of these coils is to produce variable field directions and field gradients, in order to guide and to move a catheter with magnetic material or magnetic implants for therapeutic purposes in a body, for example a human body, to be examined. However, it is not possible to achieve unrestricted navigational freedom of the magnetic body with the aid of a magnet coil system composed of six individual coils.

U.S. Pat. No. 6,241,671 describes a magnet coil system having three coils, while U.S. Pat. No. 6,529,751 B2 describes an arrangement of a few permanent magnets that are arranged rotatably about a patient and whose field can be influenced by magnetic diaphragms, and which can produce a magnetic wave for moving a magnetic probe.

Also known, furthermore, are magnet coil systems having rotatable permanent magnets for controlling magnetic catheters, in particular with radiographic monitoring.

This related art does not address methods for stabilizing position by feedback; it is assumed that in a manner prescribed by field direction and gradient a magnetic probe body always bears against an inner surface inside a body to be examined.

WO 96/03795 A1 describes a method having additional pulse coils with the aid of which a magnetic probe is to be moved in a stepwise fashion by accurately defined current pulses under computer control.

So called video capsules that serve for inspecting the digestive tract are also known, for example, from the Journal "*Gatrointestinal Endoscopy*", Vol. 54, No. 1, pages 79 to 83. In this case, the video capsule is moved by the natural intestinal movement; that is to say the movements and viewing direction are entirely random.

DE 101 42 253 C1 describes a corresponding video capsule that is equipped with a bar magnet and with video and other intervention devices. An external magnet coil system is intended to exert forces on the bar magnet for the purpose of navigation. Mention is made of a freely suspended, so-called helicopter mode with external control by a 6D mouse, a feedback of the force via the mouse, and a positional feedback by a transponder. No details emerge from the document as regards the implementation of the corresponding magnet coil system and the operation of its individual coils.

SUMMARY OF THE INVENTION

One possible object of the present invention to specify a magnet coil system that facilitates contactless navigation or movement of a (ferro)magnetic body such as, for example, a bar magnet in accordance with the abovenamed DE-C1 document. The aim in this case is for the body to be aligned in the working space and/or to exert a force on the body. The alignment and the magnitude and direction of the force on the body are intended in this case to be prescribable from outside magnetically and without mechanical connection.

The inventor proposes a magnet coil system is to serve the contactless movement of a magnetic body in a three-dimensional working space that is surrounded by surfaces defined in a rectangular x,y,z coordinate system. The coil system is to have fourteen individually drivable individual coils that are designed to produce the three magnetic field components $B_x$, $B_y$ and $B_z$ as well as five magnetic field gradients from the gradient matrix, $$D \searrow \begin{pmatrix} \frac{dB_x}{dx} & \frac{dB_y}{dx} & \frac{dB_z}{dx} \\ \frac{dB_x}{dy} & \frac{dB_y}{dy} & \frac{dB_z}{dy} \\ \frac{dB_x}{dz} & \frac{dB_y}{dz} & \frac{dB_z}{dz} \end{pmatrix} \searrow$$

which is symmetrical with reference to its diagonal D, the aim being to use the individual coils to produce two of the three diagonal elements of the gradient matrix, and to produce in each case one of the nondiagonal elements from the three gradient element pairs of the gradient matrix, which are symmetrical relative to the diagonal D.

It is assumed in the case of the magnet coil system surrounding the working space like a cage that the conditions rotH=0 and divB=0 imposed by the Maxwell equations—the variables given in bold symbolizing vectors—always produce field gradients in pairs. It was realized starting therefrom that of the possible three field components $B_x$, $B_y$ and $B_z$ only two, and of the possible nine field gradients $dB_x/dx$, $dB_x/dy$, $dB_x/dz$, $dB_y/dx$, $dB_y/dy$, $dB_y/dz$, $dB_z/dx$, $dB_z/dy$ and $dB_z/dz$ only five independent gradients need be produced. In this case, it is then necessary for eight different current patterns corresponding to the eight magnetic degrees of freedom to be capable of being impressed on the fourteen individual coils, with currents of the same magnitude. These current patterns each predominantly produce a field component or a field gradient. It is then possible by superposition to produce any combination of magnetic field components and field gradients that is permitted by the Maxwell equations.

It is possible in this way for a magnetic body to be controlled/moved (=navigated) in a contactless fashion in order to align this body in a (mechanically) contactless fashion, and/or to permit force to be exerted on it, for example a probe connected to a magnetic element such as, for example, a catheter, endoscope or a video capsule in accordance with DE 101 42 253 C1 by magnetic fields in a working space.

Thus, the fourteen individually drivable individual coils can be arranged on surfaces situated opposite in pairs, and on at least one tubular peripheral surface extending in the z direction. It is possible thereby for the surfaces to define a cuboid or cube except for the peripheral surface. However, they need not necessarily be planar. The individual coils situated on these surfaces then permit good access to the working space, in particular in the z direction.

It is advantageously possible in this case for at least six of the individual coils to be situated on the end-face or lateral surfaces, situated oppositely in pairs, of the working space, and to serve to produce the three magnetic field components $B_x$, $B_y$, $B_z$ as well as the two diagonal elements of the gradient matrix. At the same time, at least four of the individual coils can be arranged distributed as seen in the circumferential direction on the at least one tubular peripheral surface surrounding the working space, and can serve to produce at least one nondiagonal element of the gradient matrix. The required three nondiagonal elements can be formed in this way together with the remaining individual coils.

In accordance with a particularly advantageous embodiment of the coil system, it is possible for six of the individual coils to be situated as three coil pairs on the end-face or lateral surfaces, situated oppositely in pairs, of the working space, and for eight of the individual coils to form two coil arrangements that can be situated seen in the z direction one behind the other on the at least one tubular peripheral surface, and whose respectively four individual coils can be arranged distributed seen in a circumferential direction on the peripheral surface, and can serve to produce the three nondiagonal elements of the gradient matrix. This coil system is distinguished by a clear design with good accessibility to the working space in the z direction.

It is equally well possible instead of this to provide in the case of the coil system that a coil pair of individual coils is situated on the end-face surfaces of the working space, and serves to produce the magnetic field component $B_z$ as well as the diagonal element $dB_z/dz$ of the gradient matrix, that a coil arrangement composed in each case of two individual coils arranged one behind the other as seen in the z direction, is respectively situated on the lateral surfaces situated oppositely in pairs, and serves to produce the magnetic field component $B_x$ or $B_y$, that a coil arrangement composed of four individual coils arranged distributed as seen in a circumferential direction is situated on the at least one tubular peripheral surface, and that the coil arrangements on the lateral surfaces and the peripheral surface serve to produce a further diagonal element and the three nondiagonal elements of the gradient matrix.

In the embodiments described above, the field gradient coils situated on the (imaginary) peripheral surface can advantageously be fashioned in the form of a saddle. It is possible in this case for the end-face arcuate parts running on the peripheral surface in a circumferential direction to be situated next to one another as seen in this circumferential direction, that is to say to assume an angle of arc of >90° in each case, or else for them to overlap. It is easy to manufacture appropriate individual coils which produce clear field conditions.

Moreover, at least a few of the field component coils can be fashioned as flat rectangular coils or circular coils. In particular, the coils located at the end faces thus permit good access to the working space in the z direction.

Parts composed of soft magnetic material can advantageously be assigned on the outer side of the coil system for the purpose of field amplification and/or field shielding.

In order to drive the fourteen individual coils of the magnet coil system, it is advantageous to use a computer to drive its respectively assigned power supply as a function of the respective position of the magnetic body to be moved.

BRIEF DESCRIPTION OF THE DRAWINGS

These and other objects and advantages of the present invention will become more apparent and more readily appreciated from the following description of the preferred embodiments, taken in conjunction with the accompanying drawings of which:

FIG. 1 shows a first embodiment of a magnet coil system,

FIG. 2 shows in subfigures 2a to 2h, the individual coils of such a magnet coil system with current-conducting directions for producing predetermined magnetic field components and gradients, FIG. 3 shows an enlarged representation of one of the individual coils from FIG. 2, FIG. 6 shows a particular refinement of the magnet coil system in accordance with FIG. 1 having a ferromagnetic structure for field shielding and/or amplification, FIG. 7 shows a further embodiment of a magnet coil system.

DETAILED DESCRIPTION OF THE PREFERRED EMBODIMENT

Figure 4:
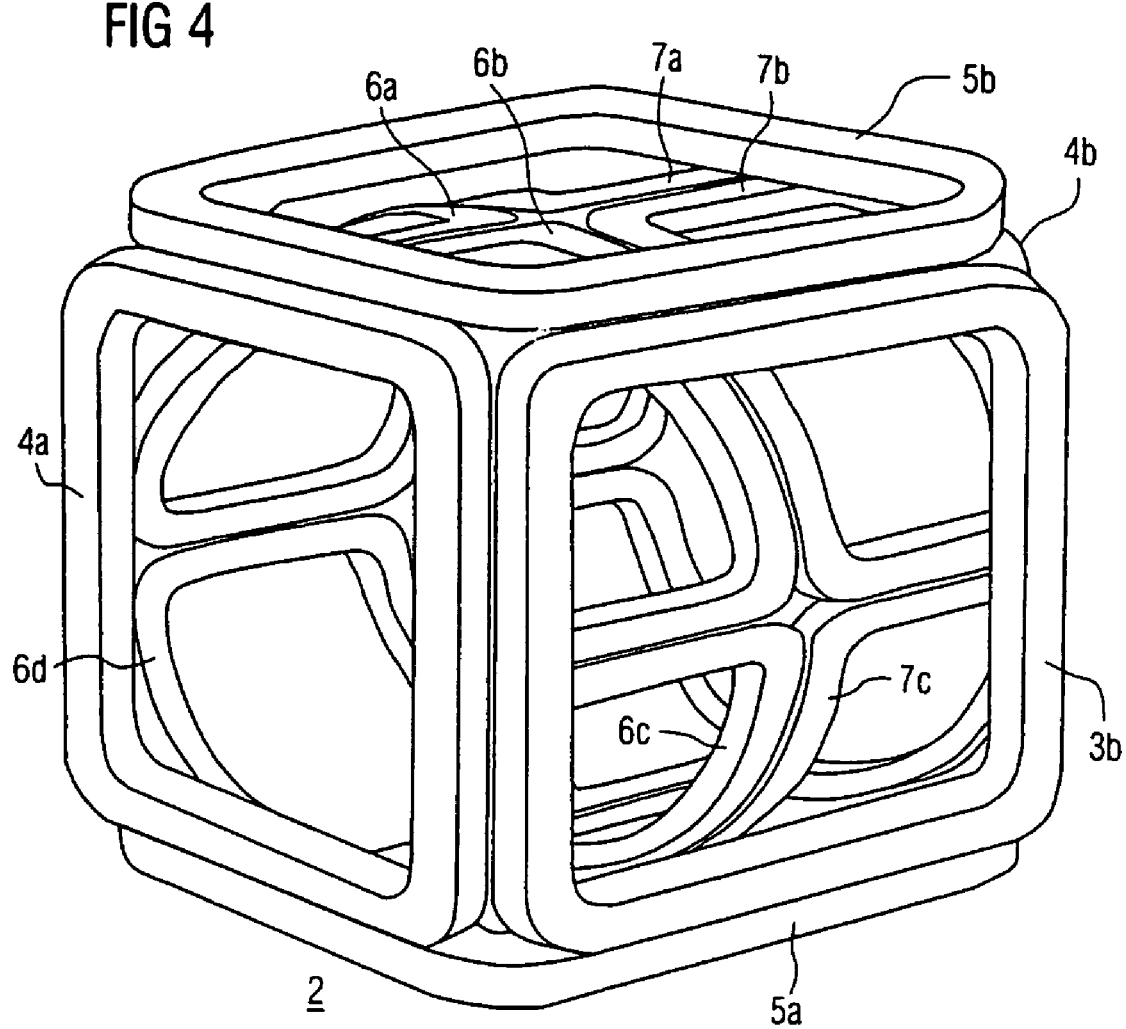
FIG. 4 shows an oblique view of the magnet coil system according to FIG. 1, constructed with conductor loops.

Reference will now be made in detail to the preferred embodiments of the present invention, examples of which are illustrated in the accompanying drawings, wherein like reference numerals refer to like elements throughout.

The inventor proposes a magnet coil system, which can be used to move a magnetic test specimen in a contactless fashion in a working volume. In this case, the alignment as well as the magnitude and direction of the force on this test specimen can be prescribed from outside magnetically and without mechanical connection. Particularly in medical applications, it is possible thereby for a probe fitted with such a magnetic test specimen to be a catheter or an endoscope having magnet elements or a small television camera with an illumination system and transmitter that transmits video images from the interior of the body such as, for example, the digestive tract or the lung. Moreover, ferromagnetic foreign bodies such as, for example, a needle or functional modules can be moved by magnetic forces in objects or spaces inaccessible from outside, or be removed therefrom. In addition to being applied in medicine, a magnet coil system can also be equally well used in other fields such as, for example in contaminated spaces. Assigned magnetic probes can also be used to inspect, for example internally, other, in particular inaccessible objects, it also being possible, of course, for the probes to be fitted with another or additional range of functions.

The magnet coil system can thus be used to control the test specimen from outside by magnetic forces in all three lateral degrees of freedom and in a viewing direction with two rotational degrees of freedom. Moreover, the magnet coil system advantageously permits access from outside in the z direction, for example in order to position persons to be treated in the interior of the working space.

FIGS. 1 to 4 show a typical exemplary embodiment of a magnet coil system with the aid of which it is possible for a ferromagnetic body to be appropriately navigated or driven and/or moved in space by having force applied to it. A probe which is assigned ferromagnetic material or which contains parts made from such a material may be selected in what follows as an exemplary embodiment of such a ferromagnetic body. The ferromagnetic body may also be denoted as a "magnet body".

The magnet coil system denoted in general by numeral 2 in FIG. 1 has, for example, an approximately cubic outer contour. The corresponding six cube faces are denoted by F3a, F3b, F4a, F4b, F5a and F5b. Let a rectangular x,y,z coordinate system be positioned in one corner of the cube. The faces F4a and F4b situated orthogonally to the z direction can be in this case be regarded as end-face surfaces, while then the pairs of surfaces F3a, F3b and F5a, F5b, respectively orthogonal to the x axis and to the y axis, can be regarded as pairs of lateral faces. The pairs of surfaces enclose an inner or working space that is denoted by A and is fashioned in three dimensions. Located in this inner space defined by the six surfaces is a tubular peripheral surface F6 having an axis running parallel to the z direction. The surfaces mentioned are generally imaginary surfaces. Of course, however, the individual coils of the magnet coil system 2 that extend on them are physical fixed by a mechanism not illustrated in the figures.

The magnet coil system 2 comprises fourteen normally conductive or superconducting individual coils that are preferably constructed as rectangular or saddle coils. In this case, the winding forms are illustrated merely schematically in the figure; it is also possible to select individual coils with rounded corners, circular coils or other forms of coil. The coil system of the selected exemplary embodiment is assembled from in this case of six field component coils 3a, 3b, 4a, 4b and 5a, 5b, as well as eight field gradient coils 6a to 6d and 7a to 7d. The field component coils 3a, 3b and 4a, 4b and 5a, 5b situated in pairs on the opposite cube faces F3a, F3b; F4a, F4b and F5a, F5b can be used to produce the field components $B_x$, $B_y$, $B_z$ as well as at least two of the three diagonal magnetic field gradients $dB_x/dx$, $dB_y/dy$ and $dB_z/dz$ from the gradient matrix reproduced below. This gradient matrix is as follows:

$$\begin{pmatrix} \frac{dB_x}{dx} & \frac{dB_y}{dx} & \frac{dB_z}{dx} \\ \frac{dB_x}{dy} & \frac{dB_y}{dy} & \frac{dB_z}{dy} \\ \frac{dB_x}{dz} & \frac{dB_y}{dz} & \frac{dB_z}{dz} \end{pmatrix}$$

Let a line joining the elements dBx/dx, dBy/dy and dBz/dz be regarded in this case as a diagonal D on the gradient matrix. The gradient matrix is constructed symmetrically with reference to this diagonal D or to the abovementioned magnetic field gradients situated on it. In this case, the sum of the diagonal elements is equal to zero. In accordance with FIG. 2 and its subfigures, the coil pairs, together with current-conducting directions to be selected in them, producing the individual field components are denoted by 3 and 4 and 5, respectively. The pairs of the field component coils are preferably arranged orthogonally relative to one another. They are generally of the same form, at least in pairs.

The field gradient coils 6a to 6d and 7a and 7d fashioned in the form of saddles are used in each case to construct two coil arrangements 6 and 7 that are arranged in series as seen in the z direction. In terms of field, the saddle-shaped field gradient coils enclose the working space A, in which case they are arranged jointly on the at least one imaginary peripheral surface F6. Seen in a circumferential direction, the gradient coils belonging to a coil arrangement are mutually spaced; that is to say there is an interspace in each case between their end-face arcuate parts and thus between their longitudinal sides running in the z direction. However, it is also possible for neighboring gradient coils to overlap with their longitudinal sides. The imaginary peripheral surface F6 has a circular cross section, for example. However, it can also have another, for example square, cross-sectional shape. Also conceivable are concentric peripheral surfaces on which the individual coils from one or from both coil arrangements are located. Neither need the at least one peripheral surface F6 necessarily be situated inside the space enclosed by the field component coils 3a, 3b, 4a, 4b, 5a, 5b, but they can also enclose the structure made from these coils, if appropriate. In general, at least the field gradient coils belonging to a coil arrangement 6 and/or 7 are of the same form.

With the aid of the field gradient coils 6a to 6d and 7a to 7d, the magnetic field gradients $dB_x/dy$, $dB_z/dx$ and $dB_z/dy$ are to be constructed in accordance with FIG. 2 and its subfigures, for example, given selection of the illustrated current-conducting directions. These three field gradients in each case constitute a nondiagonal element of the above gradient matrix. Here, these elements respectively originate from another element pair, symmetrical relative to the diagonal D. To be precise, during the construction of corresponding field gradients the field gradients symmetrical relative to the diagonal D are necessarily produced in pairs. In this case, these would be the gradients $dB_y/dx$ and $dB_x/dz$ and $dB_y/dz$, respectively. Since only five degrees of gradient freedom are to be taken into account, there is also no need for any special current pattern for the $dB_z/dz$ field gradients. As an alternative, however, it is possible to produce the $dB_z/dz$ field gradient, and in return to omit one of the gradients $dB_x/dx$ or $dB_y/dy$. That is to say, only two of the three gradients situated on the diagonal D of the gradient matrix need be produced.

If an elongated magnetic body, for example a ferromagnet or permanent magnet, that is connected to a probe, for example, is now introduced into the working space A of the magnet coil system 2, it tends to be aligned parallel to the field direction, thereby also prescribing the alignment of the probe. The field gradients in this case exert a force F=grad (m·B) on the magnetic body, m being the vector of the magnetic moment of the magnetic body. By driving each of the fourteen individual coils in a targeted fashion, it is then possible to align the magnetic body arbitrarily in the working space A, and also to exert on it a prescribed force F in all directions, that is to say the body can not only be rotated, but also moved linearly.

The subfigures 2a to 2h show in pairs the fourteen individual coils of a magnetic coil system, for example of the system 2 according to FIG. 1, in an individual illustration with the respective flow directions of the currents I for producing the field components and field gradients required for contactless movement and/or rotation. Here, in accordance with subfigures 2a and 2b, the coil pair 3 of the individual coils 3a, 3b can be used in accordance with the flow direction to produce the magnetic field component $B_x$ or the field gradient $dB_x/dx$. In a corresponding way, the individual coils 5a, 5b of coil pair 5 are to be used to form the field component $B_y$ or the field gradient $dB_y/dy$. The coil pair 4 composed of the individual coils 4a and 4b produces the field component $B_z$ in accordance with subfigure 2e. In accordance with subfigures 2f to 2h, the two coil arrangements 6 and 7 composed of the in each case four gradient coils 6a to 6d and 7a to 7d, respectively, are used according to the current-conducting direction in the individual coils to produce the field gradients $dB_z/dx$ and $dB_z/dy$ and $dB_x/dy$, respectively.

The two coil arrangements 6 and 7 from the in each case four field gradient coils 6a to 6d and 7a to 7d are illustrated in FIG. 3 in an enlarged and exploded fashion, current-conducting directions in these coils being selected in accordance with subfigure 2f.

FIG. 4 shows an oblique view of the magnetic coil system 2 according to FIGS. 1 to 3 with the conductor packets forming individual coils. It has been assumed in this case that the individual coils forming the magnetic field components $B_x$, $B_y$ and $B_z$ are, for example, situated in an approximately square shape on the six (imaginary) flat outer surfaces of a cube. Of course, these outer surfaces can also easily be of curved shape.

In addition to the field components respectively desired, each current pattern also produces other field components in the magnet coil system. These other field components are a function of the respective coil measurements and of the location of the magnetic body; their amplitude increases from the center outward in the direction of the windings of the coils. That is to say, there is thus no simple relationship between the current intensity of the current pattern with the field direction and force direction $F=\text{grad}(m \cdot B)$ at a location of the magnetic body.

However, it is possible by suitably overlapping the eight current patterns in the fourteen individual coils to set at a location of the magnetic body (probe location) precisely those fields and field gradients that produce the desired alignment and action of force on the magnetic body. It is possible with particular advantage, for example, to implement free suspension of the magnetic body in the space precisely when the weight force $F=m \cdot g=\text{grad}(m \cdot B)$ is produced (M=mass, g=acceleration due to gravity). The calculation in this regard is advantageously performed using a computer that, in particular, carries out the following computational steps and, if appropriate, repeats them continuously during a movement of the magnetic body:

calculation of the desired values for the three field components $B_x$, $B_y$, $B_z$ at the location of the magnetic body from a prescribed direction of the magnetic body in polar coordinates $\theta$ and $\phi$ in the working space, and from the modulus $|B|$;

calculation of the desired values for the five independent field gradients $dB_x/dx$, $dB_y/dy$, $dB_x/dy$, $dB_z/dx$ and $dB_z/dy$ from a prescribed magnetic force on the magnetic body; it is also possible to prescribe the gradient $dB_z/dz$ and in so doing to cause one of the other gradients $dB_x/dx$ or $dB_y/dy$ situated on the diagonal of the gradient matrix to vanish. Also conceivable are superimpositions of the gradient $dB_z/dz$ with one of the other diagonal gradients $dB_x/dx$ or $dB_y/dy$;

calculation of field components and field gradients at the location of the magnetic body for each of the eight current patterns from the coil geometry, for example for a 1 A coil current, and representation in the form of an 8×8 matrix;

calculation of an inverse matrix. This inverse matrix is a function only of the coil geometry, and can be set up in advance for each point on an array in the prescribed working space. During operation of the device, interpolation is carried out between the values in this array for the purpose of quicker calculations;

multiplication of the inverse matrix for the location of the magnetic body by the field vector ($B_x$, $B_y$, $B_z$, $dB_x/dx$, $dB_y/dy$, $dB_x/dy$, $dB_z/dx$, $dB_z/dy$) produces the current values for the eight current patterns;

dividing the current patterns over the fourteen individual coil currents in accordance in each case with a positive or negative current direction from a stored table, and linear superimposition of the currents in the individual coils;

driving the fourteen power supply units for the individual coils;

monitoring the limits of power loss in the individual coils.

Figure 5:
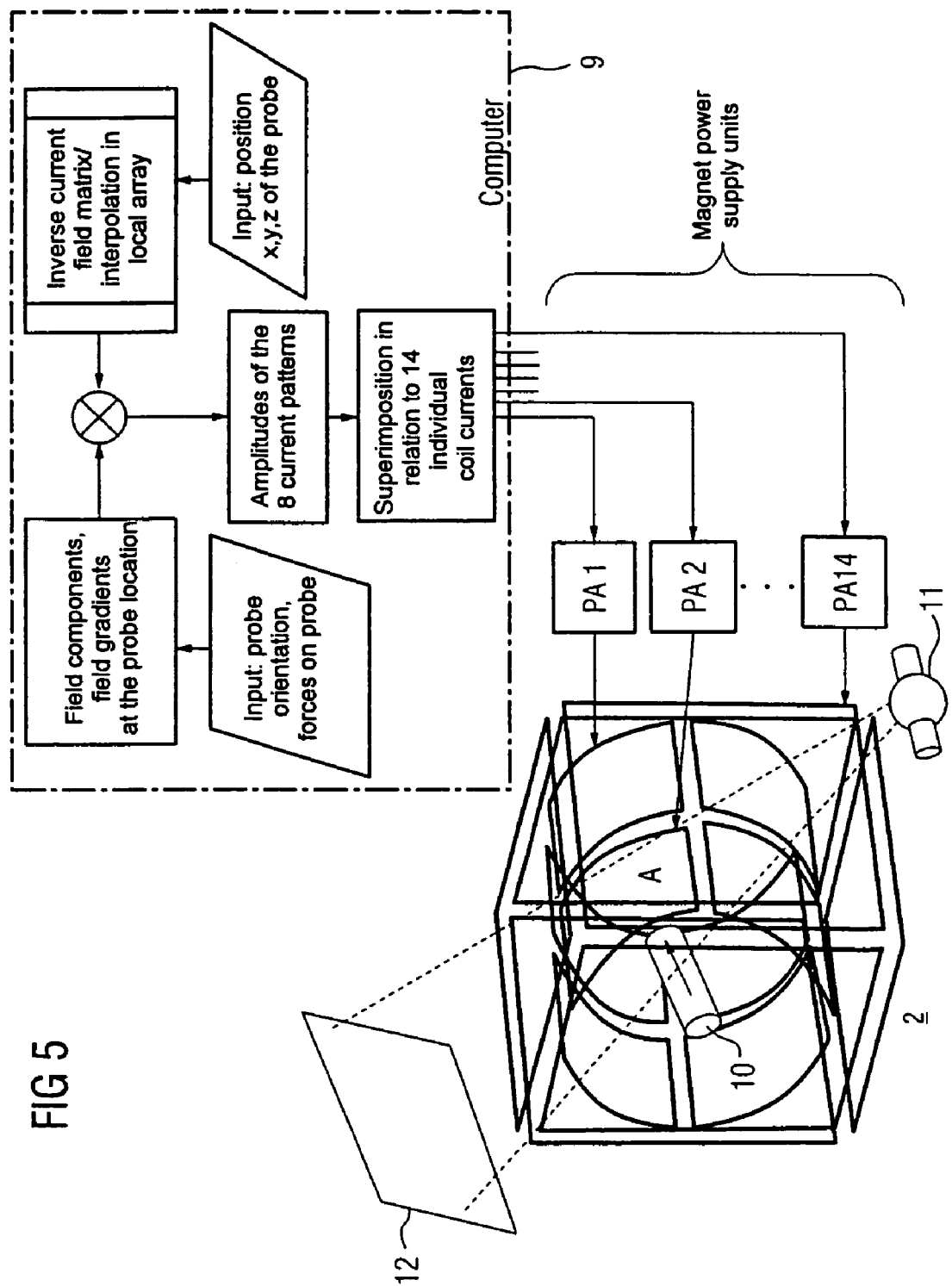
FIG. 5 shows a drive system for the individual coils of the magnet coil system in accordance with FIG. 1 by a computer.
Figure 8A:
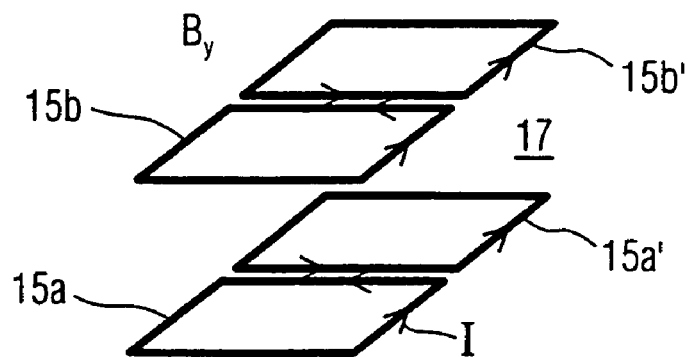
FIG. 8 shows in subfigures 8a to 8i the current-conducting directions in the individual coils of the magnet coil system according to FIG. 7.
Figure 8B:
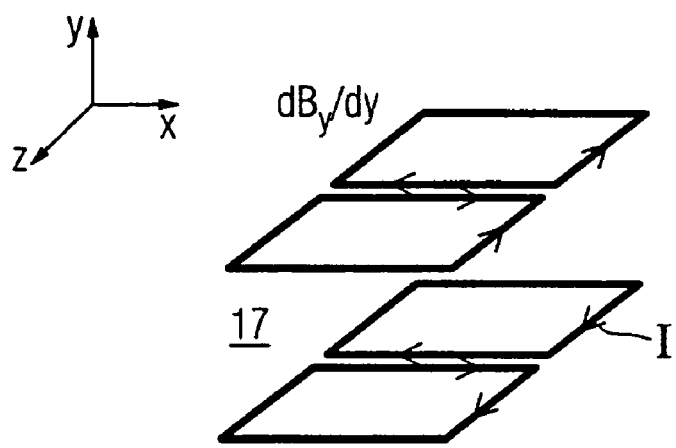
Figure 8C:
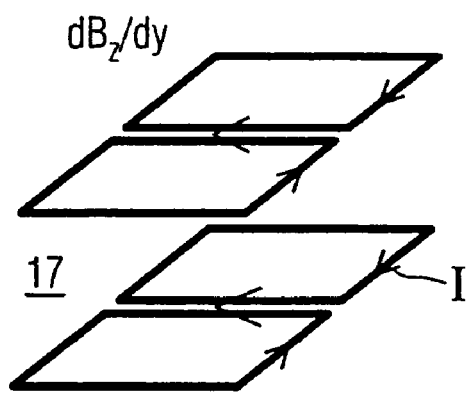
Figure 8D:
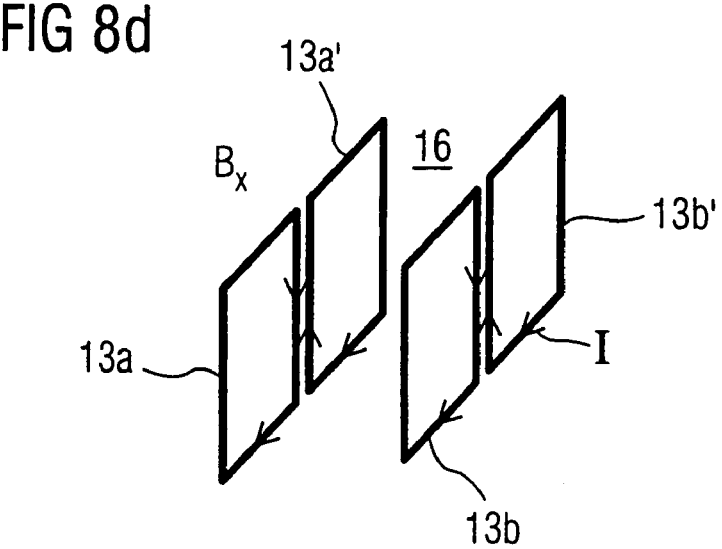
Figure 8E:
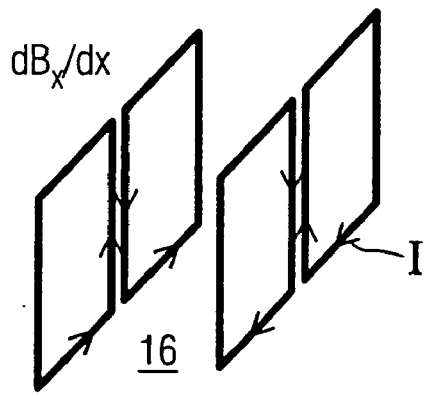
Figure 8F:
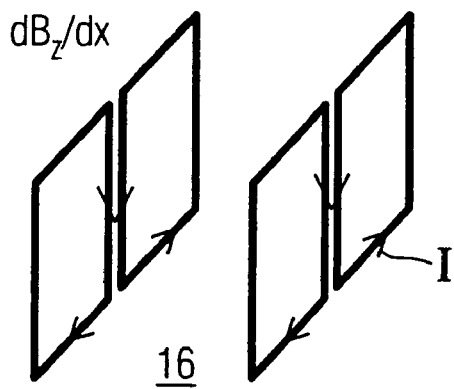
Figure 8G:
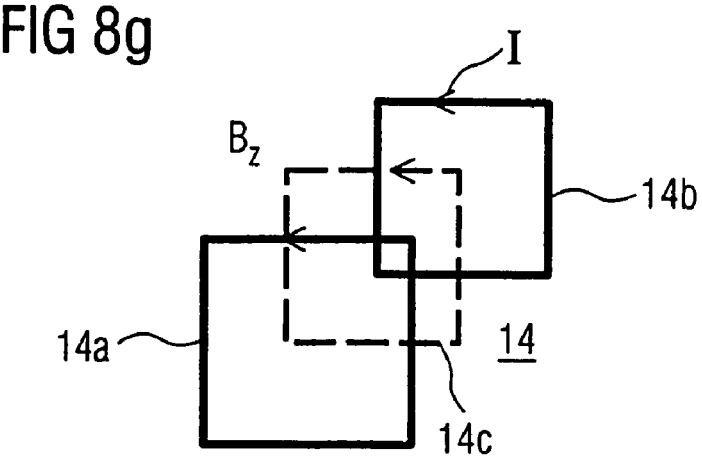
Figure 8H:
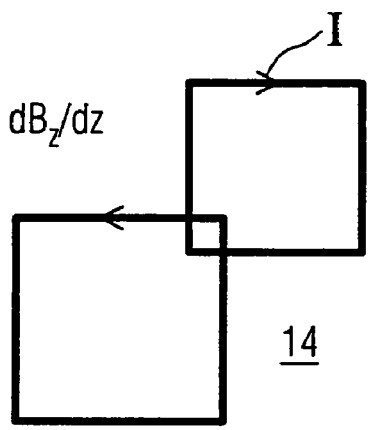
Figure 8I:
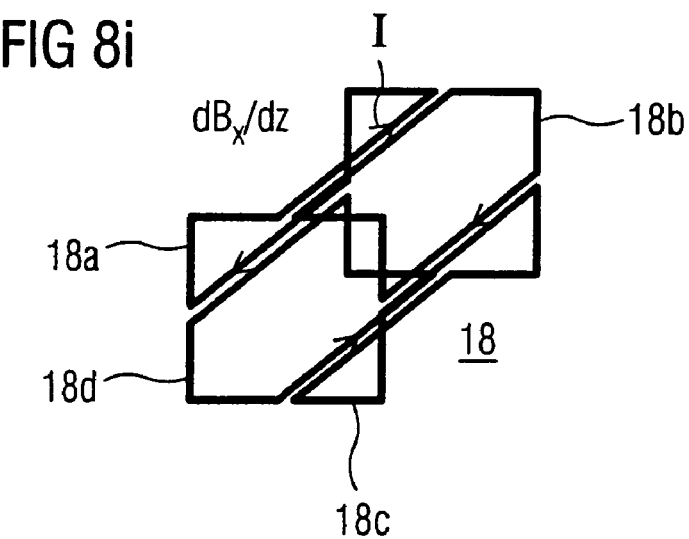

A schematic illustration of a corresponding device for driving the fourteen individual coils in cooperation with an imaging device for monitoring the position of the magnetic body or probe is to be seen in FIG. 5. A computer that drives the magnetic coil system 2 according to FIG. 1 is denoted by 9 in the figure. In addition to a freely prescribable field direction, unrestricted magnetic forces are also be exerted on a magnetic body or a corresponding probe 10 in all three spatial directions with the aid of the fourteen individual coils of the magnet coil system. The fourteen power supply units, driven by the computer 9, for the fourteen individual coils are denoted by PA1 to PA14. Furthermore, the figure also indicates an X-ray tube 11 of an X-ray unit whose radiation transradiates the free space between the windings of the individual coils. The position or movement of the magnetic body 10 is then to be observed on a display screen 12 outside the magnet coil system.

The following measures can be provided for the purpose of a specific configuration of the magnet coil system in accordance with the illustrations in the figures:

The individual coils can be wound from aluminum or copper strip and be liquid-cooled, if appropriate.

The individual coils can be fabricated from hollow metal profiles through the interior of which a cooling medium is led, if appropriate.

In particular, the individual coils can be made from superconducting conductors, preferably with the aid of a high-$T_c$ superconductor material.

Of course, further individual coils can also be used, for example, to homogenize the magnetic field. A corresponding individual coil is indicated by dashes in subfigure 2e and denoted by 4c. It homogenizes the field component $B_z$ in space.

Moreover, magnetic material can be assigned to the magnet coil system. For example, the system may be surrounded at least partly by parts made from such material. A corresponding configuration follows from FIG. 6 for the magnet coil system 2 according to FIG.

1. According thereto, magnetic return bodies 19i made from soft magnetic material such as iron are provided; they surround the gradient coils of the system 2 from the outside. Field amplification in the working space A and/or stray field shielding to the outside, in particular, can be achieved with such soft magnetic parts.

If appropriate, it is possible to select different conductor cross sections for the individual coils of a coil pair in order to produce the magnetic field components or a coil arrangement for producing the field gradients. Thus, for example, an upper y individual coil, for example the individual coil 5b according to subfigure 2c, can have a larger conductor cross section or an increased number of turns per unit length by comparison with the lower y coil 5a assigned to it. Of course, such a different configuration is also possible for the other coil pairs and/or coil arrangements.

In the case of the exemplary embodiments, illustrated in the above figures, of the magnetic coil system 2, it has been assumed that in addition to the field components $B_x$, $B_y$ and $B_z$ the field component coils arranged orthogonally in pairs on opposite faces of a cube can also be used to produce two of the three diagonal field gradients in accordance with the above gradient matrix. However, it is possible, furthermore, also to use field component coils to generate nondiagonal field gradients. It is necessary for this purpose that at least one, in particular two of the three field component coils are formed by coil pairs composed of individual coils. Such an embodiment can be provided, for example, whenever the magnet coil system has a squarer contour around a working space. A corresponding exemplary embodiment of a magnet coil system having, in turn, fourteen individual coils is indicated in FIGS. 7 and 8 in the representation corresponding to FIGS. 1 and 2, and denoted by 20. Here, the subfigures 8a to 8i show the current-conducting directions to be selected in the individual coils for the magnetic field components and gradients. In the case of this embodiment, a coil pair 14 composed of individual coils 14a and 14b is situated on end-face surfaces F14a and F14b of the working space A. In accordance with subfigures 8g and 8h, the magnetic field component $B_z$ and the associated gradient element $dB_z/dz$ can be produced on the diagonal D of the gradient matrix with the aid of these, for example circularly, individual coils. By contrast, the field component coils to be arranged on lateral surfaces F13a, F13b and F15a, F15b situated opposite in pairs are formed in each case by a coil arrangement 16 or 17, respectively, composed in each case of two individual coils arranged in series as seen in the z direction. In accordance with subfigure 8d, the coil arrangement 16 is assembled in this case from the individual coils 13a, 13a' as well as 13b and 13b', respectively. In accordance with subfigures 8d, 8e and 8f, the field component $B_x$ or the diagonal gradient element $dB_x/dx$ or the nondiagonal gradient element $dB_z/dx$ are then to be produced in these individual coils depending on the current-conducting direction. In accordance with subfigures 8a to 8c, it is possible in a corresponding way to use the individual coils 15a, 15a' and 15b, 15b' of the coil arrangement 17 on the lateral surfaces F15a and F15b to produce the field component $B_y$ or the diagonal gradient element $dB_y/dy$ or the nondiagonal gradient element $dB_z/dy$. In order to be able to produce the third one of the nondiagonal gradient elements $dB_x/dy$ in accordance with FIG. 8i, there is also a need for a further coil arrangement 18 composed of four individual coils 18a to 18d. These individual coils are situated on an (imaginary) tubular peripheral surface F18, extending parallel to the z axis and enclosing the working space A, inside the contour formed by the field component coils. These four individual coils 18a to 18d are arranged in a uniformly distributed fashion as seen in the circumferential direction of the peripheral surface F18, it being possible, if appropriate, for their longitudinal sides running in the z direction to overlap. A square cross-sectional shape has admittedly been assumed for the imaginary peripheral surface in the illustration according to subfigure 8i. However, as may be seen from FIG. 7, it is also possible to provide other shapes for this purpose. Furthermore, in the subfigure 8g, the possibility, also addressed in relation to subfigure 2e, is indicated of providing further individual coils for the purpose of homogenizing the magnetic field. Thus, an appropriate homogenization of the field component $B_z$ can be achieved with the aid of the individual coil denoted by 14c and executed with dashes in the subfigure.

In the representation of the embodiment of a magnetic coil system 20 in FIGS. 7 and 8, it has been assumed that all three diagonal gradient elements are to be produced. However, since only two of these elements are required, it is possible to dispense with one of the corresponding current patterns of subfigures 8b, 8e and 8h. It is of no importance here which current pattern is omitted. Moreover, it is also possible to produce only one gradient in accordance with subfigures 8b, 8e and 8h. The second gradient can then be formed by a linear combination of the two other gradients, the ratio of the coil currents being fixed and independent of the current value. That is to say, it is always possible to produce gradients by an appropriate linear combination of the coil currents from various individual coils. This is also valid, of course, for the embodiment of the magnet coil system 2 according to FIGS. 1 and 2.

The invention has been described in detail with particular reference to preferred embodiments thereof and examples, but it will be understood that variations and modifications can be effected within the spirit and scope of the invention covered by the claims which may include the phrase "at least one of A, B and C" or a similar phrase as an alternative expression that means one or more of A, B and C may be used, contrary to the holding in *Superguide* v. *DIRECTV,* 69 USPQ2d 1865 (Fed. Cir. 2004).

What is claimed is:

1. A magnet coil system for contactless movement of a magnetic body in a three-dimensional working space, comprising:

fourteen individually drivable coils that are designed to produce three magnetic field components $B_x$, $B_y$ and $B_z$ as well as five magnetic field gradients selected from the gradient matrix:

$$\begin{pmatrix} \dfrac{dB_x}{dx} & \dfrac{dB_y}{dx} & \dfrac{dB_z}{dx} \\ \dfrac{dB_x}{dy} & \dfrac{dB_y}{dy} & \dfrac{dB_z}{dy} \\ \dfrac{dB_x}{dz} & \dfrac{dB_y}{dz} & \dfrac{dB_z}{dz} \end{pmatrix}$$

the gradient matrix having a diagonal with three gradients on the diagonal, each gradient on the diagonal having a gradient element pair formed from two off-diagonal gradients, which are symmetrical with respect to the gradient on the diagonal, the matrix having three gradient element pairs, the five magnetic field gradients being two of the three gradients on the diagonal, and three off-diagonal gradients, one off-diagonal gradient from each of the three gradient element pairs.

2. The system as claimed in claim 1, wherein the fourteen individually drivable coils are arranged in pairs on opposite planes about the three-dimensional working space, and are arranged in a tubular peripheral configuration extending in a z direction.

3. The coil system as claimed in claim 2, wherein
at least six of the coils are arranged in pairs on opposite planes about the three-dimensional working space,
the coils on the opposite planes serve to produce the three magnetic field components $B_x$, $B_y$, $B_z$ as well as the two diagonal elements of the gradient matrix,
at least four of the coils are distributed circumferentially in a tubular peripheral configuration surrounding the working space, and
the coils distributed in a circumferential direction serve to produce at least one off-diagonal gradient.

4. The coil system as claimed in claim 1, wherein
six of the coils are arranged in pairs on opposite planes about the three-dimensional working space,
eight of the coils form two coil arrangements having four coils each situated in a z direction one behind another, each coil arrangement having the four coils distributed circumferentially in a tubular peripheral configuration, and
the coils that form the two coil arrangements serve to produce the three off-diagonal gradients.

5. The coil system as claimed in claim 3, wherein
a z-pair of coils is arranged respectively on a pair of planes, which are orthogonal to a z-axis of the working space,
the z-pair of coils serves to produce the magnetic field component $B_z$ as well as the diagonal gradient $dB_z/dz$,
a lateral coil arrangement has four coils with two coil pairs, the coil pairs being arranged in opposite planes, each coil pair having coils arranged one behind another as seen in the z direction,
the lateral coil arrangement serves to produce the magnetic field component $B_x$ or $B_y$,
a circumferential coil arrangement is formed of four coils distributed circumferentially in a tubular peripheral configuration, and
the lateral coil arrangement serves to produce a diagonal gradient other than $dB_z/dz$ and serves to produce the three off-diagonal gradients.

6. The coil system as claimed in claim 2, wherein
the working space has x, y, and z axes,
coils are selectively provided in six planes provided in opposing pairs to enclose the working space, each plane being orthogonal to one of the x, y and z directions,
coils are selectively distributed circumferentially in a tubular peripheral configuration about the z axis, and
the coils distributed circumferentially in the tubular peripheral configuration are positioned on an interior of the working space with respect to the coils provided in six planes.

7. The coil system as claimed in claim 2, wherein the coils arranged in the tubular peripheral configuration are fashioned in the form of a saddle.

8. The coil system as claimed in claim 7, wherein the coils arranged in the tubular peripheral configuration are situated next to one another or overlaping, as seen in a circumferential direction.

9. The coil system as claimed in claim 1, wherein a plurality of the coils are fashioned as flat rectangular coils or circular coils.

10. The coil system as claimed in claim 3, wherein the coils arranged in pairs on opposite planes and/or the coils distributed circumferentially in the tubular peripheral configuration are identical to one another.

11. The coil system as claimed in claim 2, wherein the coils arranged in pairs on opposite planes produce the magnetic field components.

12. The coil system as claimed in claim 1, further comprising parts composed of a soft magnetic material positioned on an exterior of the working space with respect to the coils, for field amplification and/or field shielding.

13. The coil system as claimed in claim 1, further comprising a device to detect a position of the magnetic body inside the working space.

14. The coil system as claimed in claim 1, further comprising a computer-aided device to drive the coils.

15. The coil system as claimed in claim 3, wherein
six of the coils are arranged in pairs on opposite planes about the three-dimensional working space,
eight of the coils form two coil arrangements having four coils each situated in a z direction one behind another, each coil arrangement having the four coils distributed circumferentially in a tubular peripheral configuration, and
the coils that form the two coil arrangements serve to produce the three off-diagonal gradients.

16. The coil system as claimed in claim 15, wherein
the working space has x, y, and z axes,
coils are selectively provided in six planes provided in opposing pairs to enclose the working space, each plane being orthogonal to one of the x, y and z directions,
coils are selectively distributed circumferentially in a tubular peripheral configuration about the z axis, and
the coils distributed circumferentially in the tubular peripheral configuration are positioned on an interior of the working space with respect to the coils provided in six planes.

17. The coil system as claimed in 16, wherein the coils arranged in the tubular peripheral configuration are fashioned in the form of a saddle.

18. The coil system as claimed in claim 17, wherein the coils arranged in the tubular peripheral configuration are situated next to one another or overlaping, as seen in a circumferential direction.

19. The coil system as claimed in claim 18, wherein a plurality of the coils are fashioned as flat rectangular coils or circular coils.

20. The coil system as claimed in claim 19, wherein the coils arranged in pairs on opposite planes and/or the coils distributed circumferentially in the tubular peripheral configuration are identical to one another.

21. The coil system as claimed in claim 20, wherein the coils arranged in pairs on opposite planes produce the magnetic field components.

22. The coil system as claimed in claim 21, further comprising parts composed of a soft magnetic material positioned on an exterior of the working space with respect to the coils, for field amplification and/or field shielding.

23. The coil system as claimed in claim 22, further comprising a device to detect a position of the magnetic body inside the working space.

24. The coil system as claimed in claim 23, further comprising a computer-aided device to drive the coils.

25. A magnet coil system for contactless movement of a magnetic body in a three-dimensional working space, comprising:

a plurality of individually drivable individual coils that are designed to produce three magnetic field components $B_x$, $B_y$ and $B_z$ as well as five magnetic field gradients selected from the gradient matrix:

$$\begin{pmatrix} \dfrac{dB_x}{dx} & \dfrac{dB_y}{dx} & \dfrac{dB_z}{dx} \\ \dfrac{dB_x}{dy} & \dfrac{dB_y}{dy} & \dfrac{dB_z}{dy} \\ \dfrac{dB_x}{dz} & \dfrac{dB_y}{dz} & \dfrac{dB_z}{dz} \end{pmatrix}$$

the gradient matrix having a diagonal with three gradients on the diagonal, each gradient on the diagonal having a gradient element pair formed from two off-diagonal gradients, which are symmetrical with respect to the gradient on the diagonal, the matrix having three gradient element pairs, the five magnetic field gradients being two of the three gradients on the diagonal, and three off-diagonal gradients, one off-diagonal gradient from each of the three gradient element pairs.

26. A magnetic coil system comprising:

a plurality of coils arranged about a working space having x, y, and z axes, such that:

coils are selectively provided in six planes provided in opposing pairs to enclose the working space, each plane being orthogonal to one of the x, y and z directions; and coils are selectively distributed circumferentially in a tubular peripheral configuration about the z axis, wherein in one of the opposing pairs of planes, coils are arranged one behind another, displaced in the direction to which the planes are orthogonal, or, in the tubular circumferential direction, coils are arranged one behind another, displaced in the z direction, wherein the magnetic coil system further comprises a driving device to drive the coils to produce gradients selected from the gradient matrix:

$$\begin{pmatrix} \dfrac{dB_x}{dx} & \dfrac{dB_y}{dx} & \dfrac{dB_z}{dx} \\ \dfrac{dB_x}{dy} & \dfrac{dB_y}{dy} & \dfrac{dB_z}{dy} \\ \dfrac{dB_x}{dz} & \dfrac{dB_y}{dz} & \dfrac{dB_z}{dz} \end{pmatrix}$$

wherein the gradient matrix has a diagonal with three gradients on the diagonal, each gradient on the diagonal having a gradient element pair formed from two off-diagonal gradients, which are symmetrical with respect to the gradient on the diagonal, the gradient matrix having three gradient element pairs, and wherein the driving device drives the coils which are arranged one behind another to produce three off-diagonal gradients, one off diagonal element from each of the three gradient element pairs.

* * * * *

UNITED STATES PATENT AND TRADEMARK OFFICE
CERTIFICATE OF CORRECTION

| | | |
|---|---|---|
| PATENT NO. | : 7,173,507 B2 | Page 1 of 1 |
| APPLICATION NO. | : 10/934738 | |
| DATED | : February 6, 2007 | |
| INVENTOR(S) | : Günter Ries | |

It is certified that error appears in the above-identified patent and that said Letters Patent is hereby corrected as shown below:

Column 11, Line 61, after "in" insert --claim--.

Signed and Sealed this

Twenty-second Day of May, 2007

JON W. DUDAS
*Director of the United States Patent and Trademark Office*